(12) United States Patent
Widmer

(10) Patent No.: US 7,014,010 B2
(45) Date of Patent: Mar. 21, 2006

(54) METHOD FOR MANUFACTURING AN EAR DEVICE AND EAR DEVICE

(75) Inventor: Christoph Widmer, Stäfa (CH)

(73) Assignee: Phonak AG, Stafa (CH)

( * ) Notice: Subject to any disclaimer, the term of this patent is extended or adjusted under 35 U.S.C. 154(b) by 364 days.

(21) Appl. No.: 09/982,290

(22) Filed: Oct. 17, 2001

(65) Prior Publication Data

US 2004/0069560 A1  Apr. 15, 2004

Related U.S. Application Data

(63) Continuation-in-part of application No. 09/670,207, filed on Sep. 25, 2000, now Pat. No. 6,540,045, which is a continuation-in-part of application No. 09/607,701, filed on Jun. 30, 2000, now abandoned.

(51) Int. Cl.
*H04R 25/02* (2006.01)

(52) U.S. Cl. ................. 181/130; 181/135; 381/328
(58) Field of Classification Search ........... 181/120, 181/130, 135; 381/328, 329, 322
See application file for complete search history.

(56) References Cited

U.S. PATENT DOCUMENTS

| | | | | |
|---|---|---|---|---|
| 5,056,204 A | * | 10/1991 | Bartschi | 29/896.21 |
| 5,185,802 A | * | 2/1993 | Stanton | 181/129 |
| 5,487,012 A | | 1/1996 | Topholm et al. | |
| 5,781,637 A | * | 7/1998 | Heide et al. | 381/328 |
| 2002/0133080 A1 | * | 9/2002 | Apruzzese et al. | 600/477 |
| 2003/0100819 A1 | * | 5/2003 | Newman et al. | 600/300 |

FOREIGN PATENT DOCUMENTS

| | | |
|---|---|---|
| BE | 1 010 200 A | 3/1998 |
| DE | 40 41 105 A | 6/1992 |
| WO | 01 05207 A | 1/2001 |

* cited by examiner

*Primary Examiner*—Marlon T. Fletcher
*Assistant Examiner*—David Warren
(74) *Attorney, Agent, or Firm*—Pearne & Gordon LLP

(57) ABSTRACT

A hearing device, which is to be applied to an area of an individual's ear, is manufactured in that the skin of that application area is first analyzed and the outer surface area of the hearing device is adapted to the characteristics of that skin, thereby taking into account the result of said analyzing. Analyzing may preferably be directed on characteristics of visual appearance, surface structure, chemical surface characteristics, mechanical behavior and state of health of such skin.

6 Claims, 13 Drawing Sheets

METHOD FOR MANUFACTURING AN EAR DEVICE AND EAR DEVICE

This application is a Continuation-In-Part of U.S. application Ser. No. 09/670,207 filed Sep. 25, 2000, now U.S. Pat. No. 6,540,045 which is a Continuation-In-Part of U.S. application Ser. No. 09/607,701 filed Jun. 30, 2000 now abandoned.

The present invention relates to a method defined in the preamble of claim 1 and to an ear device defined in the preamble of claim 6.

The present invention is based on the problems arising in manufacturing of in-ear hearing aids. However, the solution as found is generally applicable to ear devices as defined further below.

When manufacturing hearing aid shells today typically audiologists produce a model of the shape of the individual auditory canals, thereby taking a mold thereof, typically of silicon. This model is then sent to the hearing aid manufacturer who on the basis of this basis casts a hearing aid shell from a plastic material.

This procedure is problematic under different aspects:

Based on the mold plastic materials must be used for the shell making, which result in a shell which is relatively hard and stable with respect to its shape. This as a result leads to the fact that when inserting the finished in-ear hearing aid into an individual's ear, on account of the remaining pressure spots, the shell of the hearing aid must practically always be refinished.

Even though the above procedure allows making the resulting relatively hard shell with an outer shape matching the mold, it does not allow making complex inner and/or outer shapes such as would be desirable for configuring in an optimal manner the shape of mounts for the hearing aid's functional components. We understand under the expression "functional components" all units which are provided for reception, processing and reproduction of audio signals, that is, microphones, digital processor units, loudspeakers and accessories such as remote controls, binaural signal transmissions, batteries, etc. It must additionally be borne in mind that optimal packaging of such functional components using the space available can only be realized on an individual basis, because the geometry of the auditory canal are substantially different from individual to individual.

The above-mentioned procedure is on one hand highly labor intensive and on the other hand the resulting hearing aid will mostly be less than optimal with respect to comfort of wear and space utilization. The material used in this conventional manufacturing furthermore necessitates a relatively thick wall of the in-ear hearing aid shell, thereby further and additionally reducing the space available for implementing the functional components.

The objective of the present invention is to eliminate these drawbacks. To that end the invention is characterized in that at least one shape of the application area for the device is three-dimensionally digitized to result in a set of data and that the ear device or its shell is realized by an additive built-up process controlled by the set of data. Even though this manufacturing method is particularly appropriate for in-ear hearing aids, it also may be used with comparable advantages for outside-the-ear hearing aids, further for for other ear devices, as e.g. for manufacturing earphones of all kinds, water-protection inserts, noise-protection inserts etc. In a preferred embodiment of the method according to the present invention account is taken that the area where the ear device is applied to the individual—think in particular of in-ear ear devices—undergoes a substantial dynamic in everyday life, for instance the auditory canal during chewing. By registering a single shape of the area of application of the device, so to speak as a snapshot, such dynamics cannot be taken into account for manufacturing the ear device. According to a preferred embodiment of the method according to the present invention, it registers more than one shape of the individual area of application of the device during its natural motion or at distinct positions out of that natural motion similarly to registering a movie of the dynamics of the application area, and it controls the additive built-up process in function of the data set so obtained.

The manufacturing method according to the present invention and an ear device realized thereby are exemplified below also with the help of figures. Therein:

Figure 4:
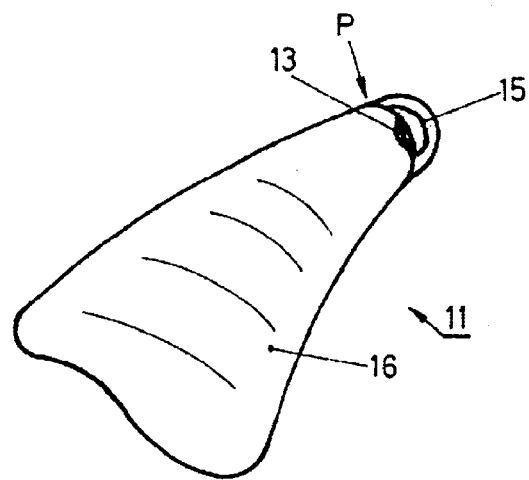
Figure 5:
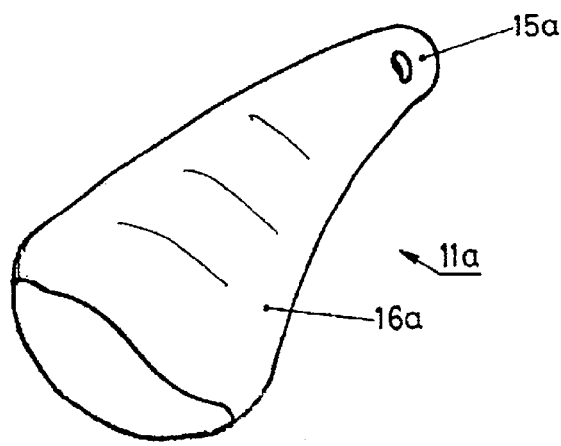
Figure 6:
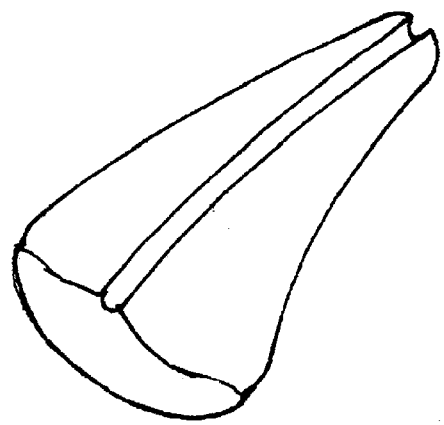
Figure 7:
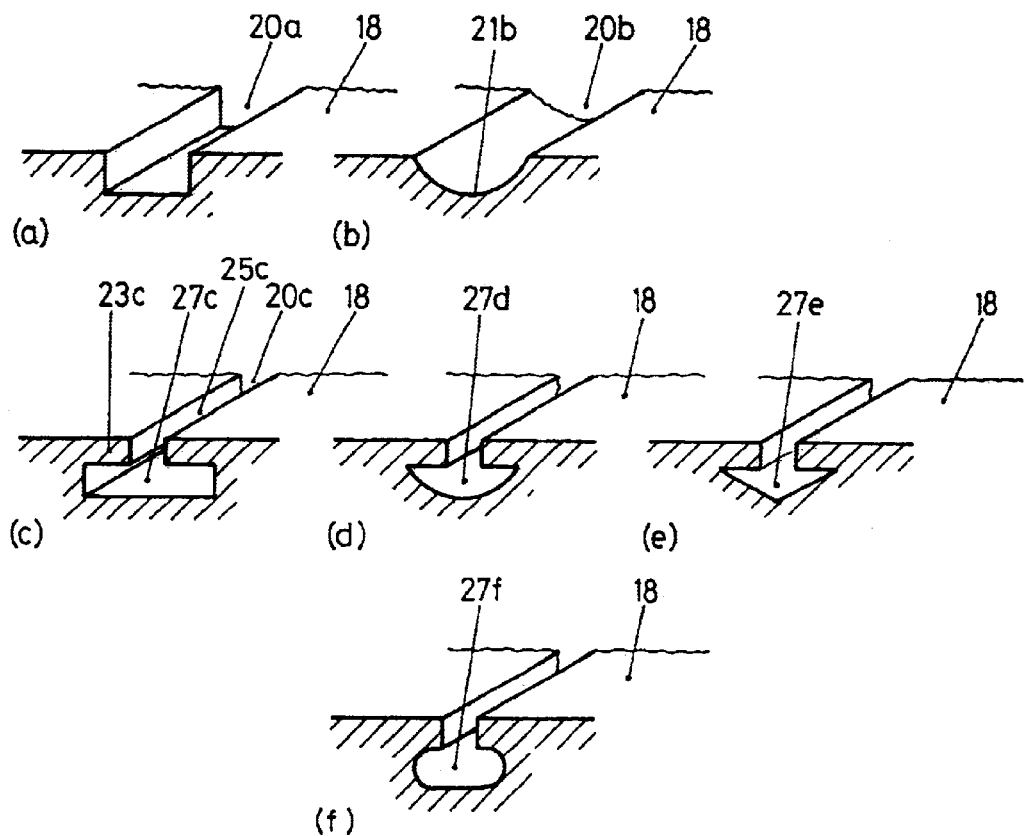
Figure 8:
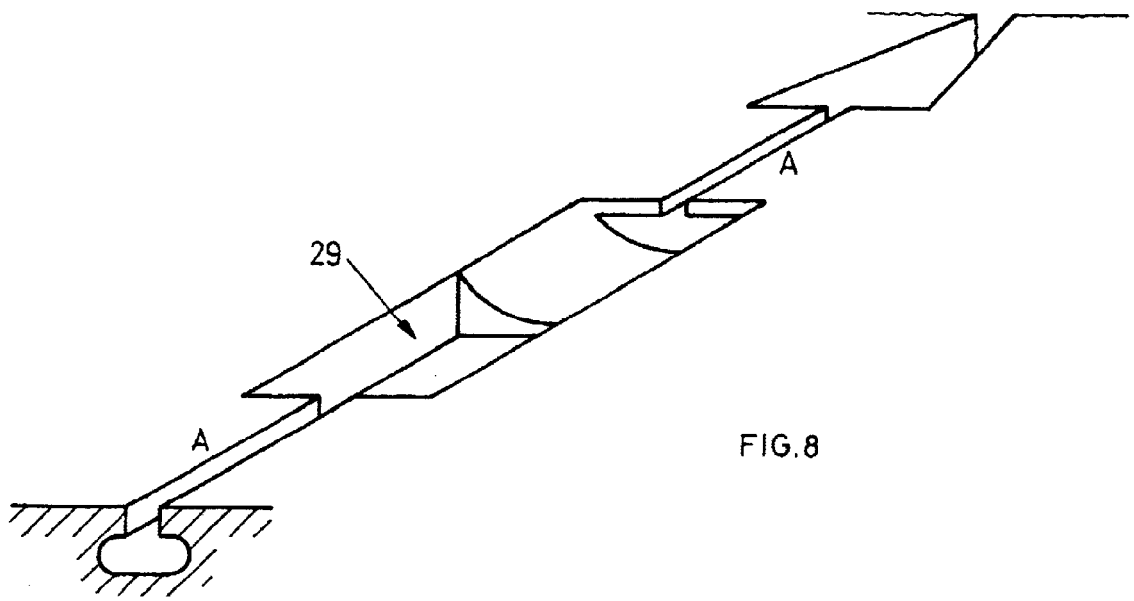
Figure 9:
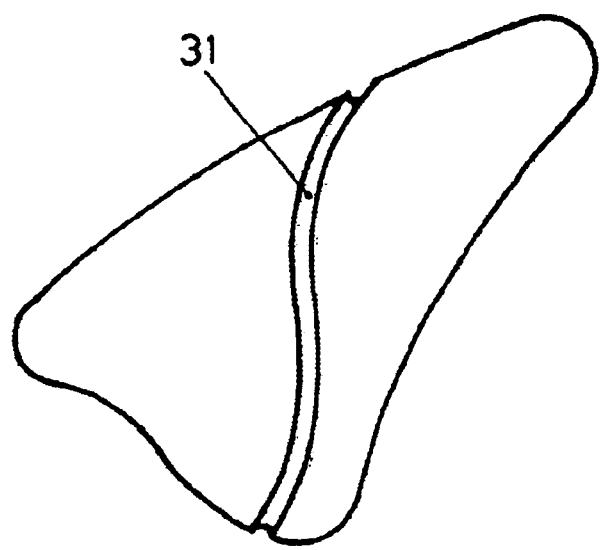
Figure 10:
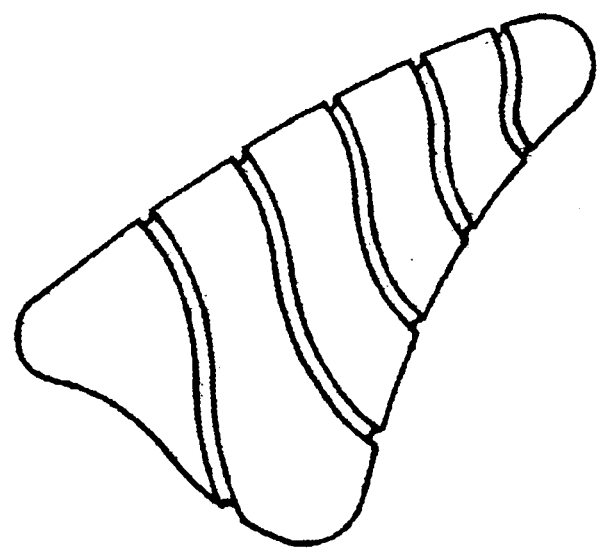
Figure 11:
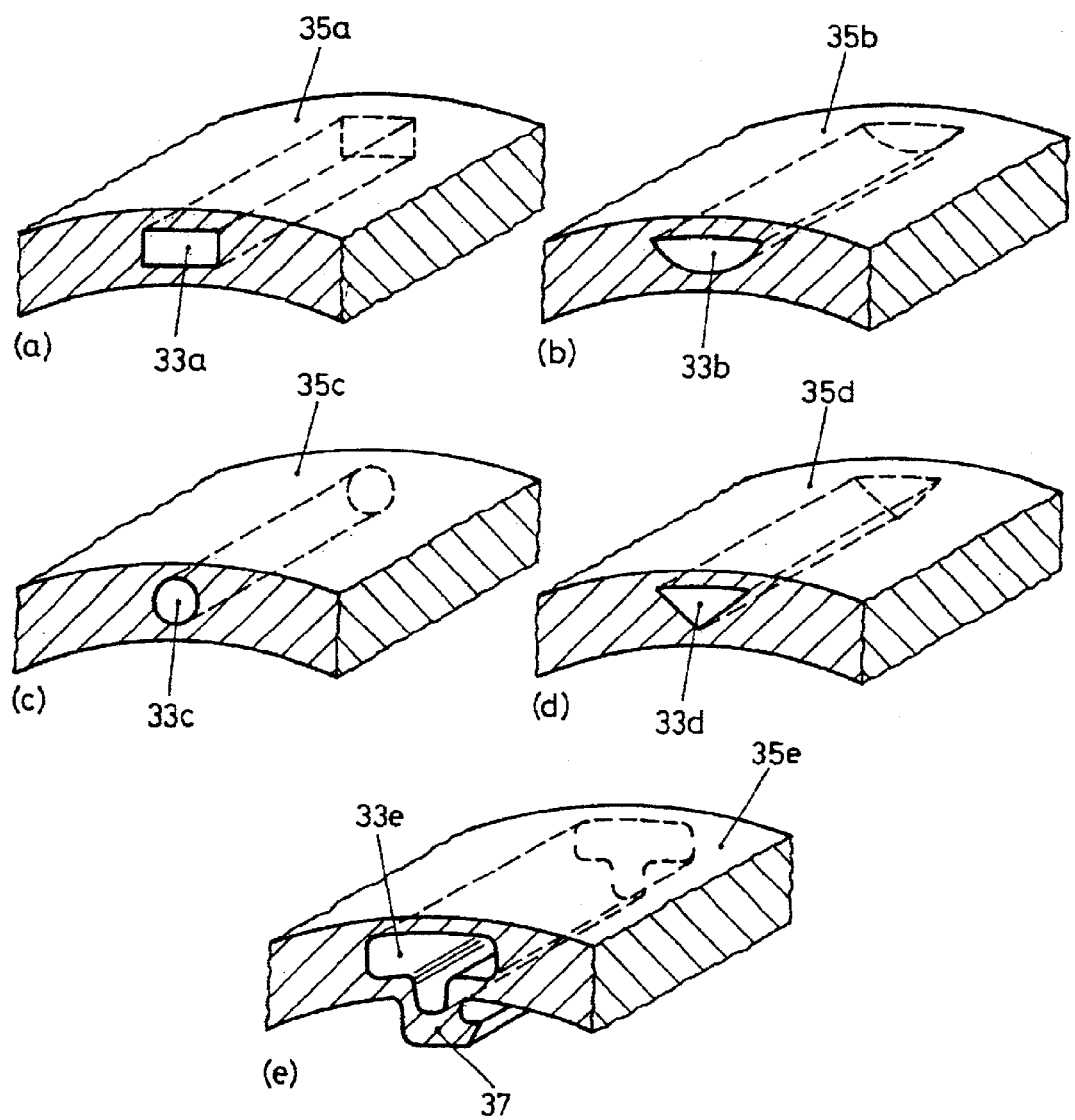
Figure 12:
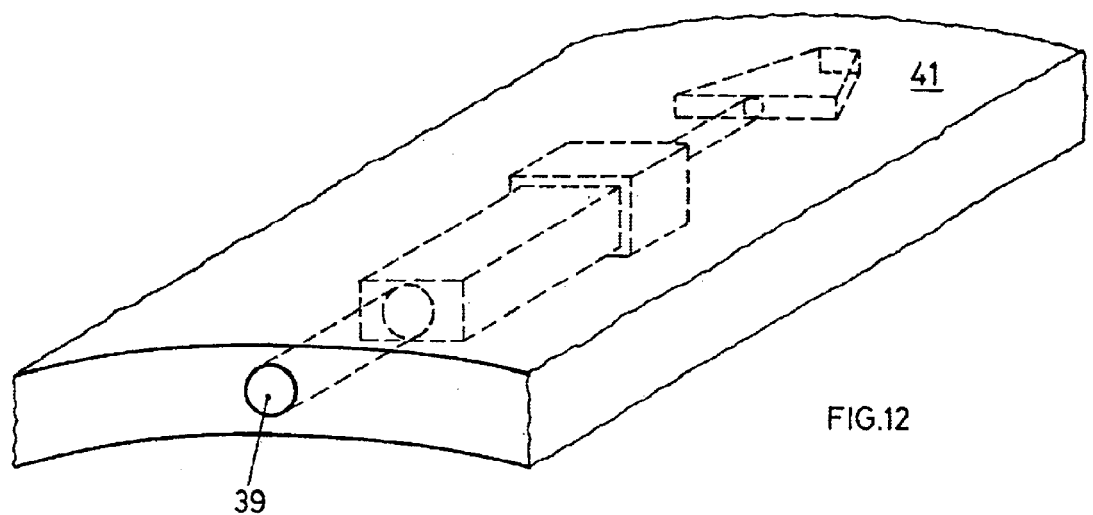
Figure 13:
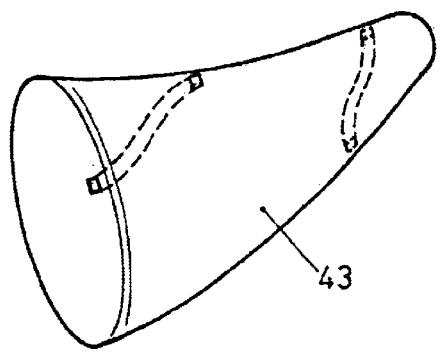
Figure 14:
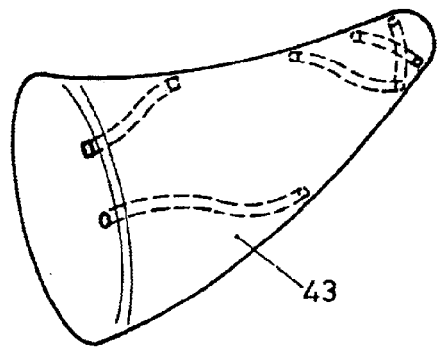
Figure 15:
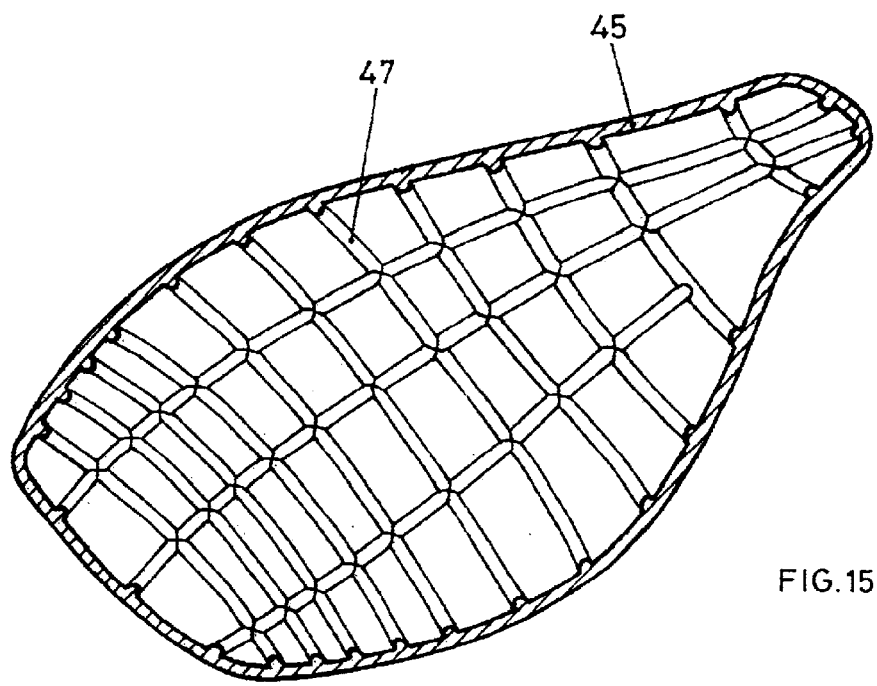
Figure 16:
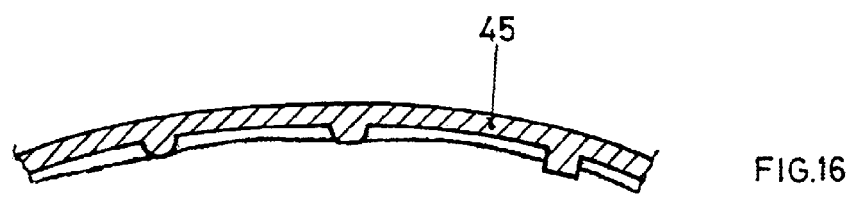
Figure 17:
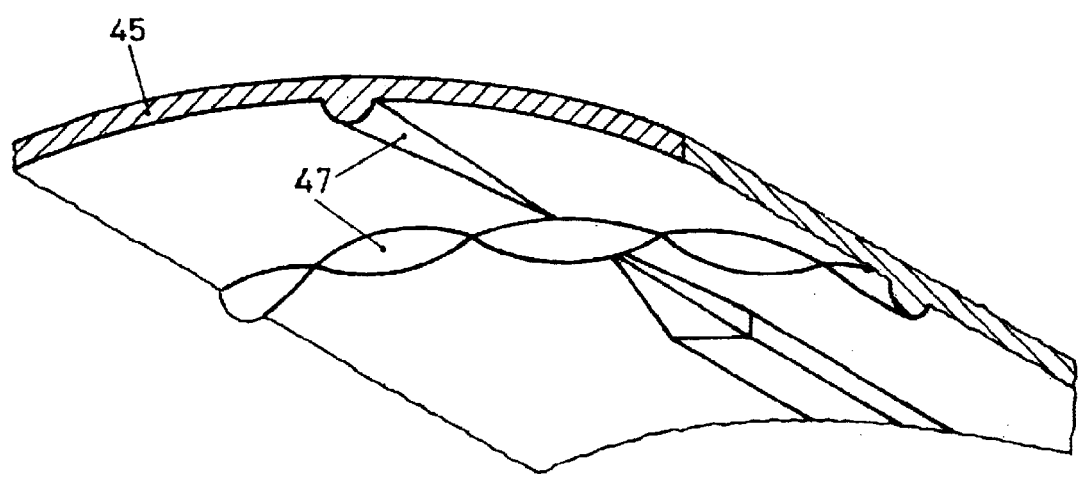
Figure 18:
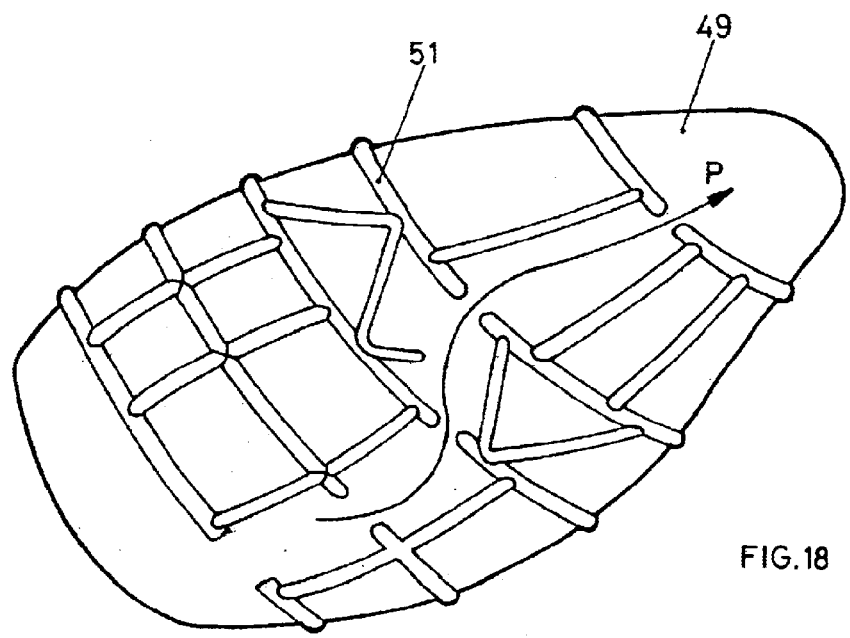
Figure 19:
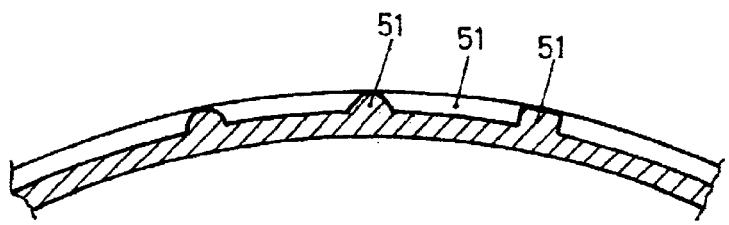
Figure 20:
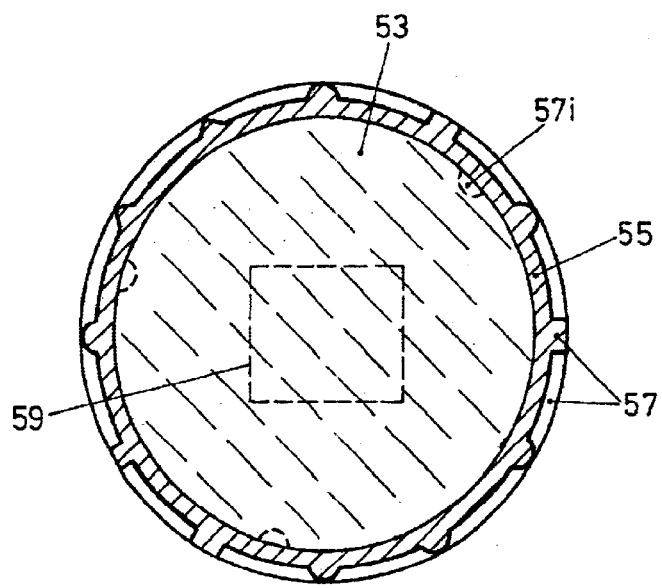
Figure 21:
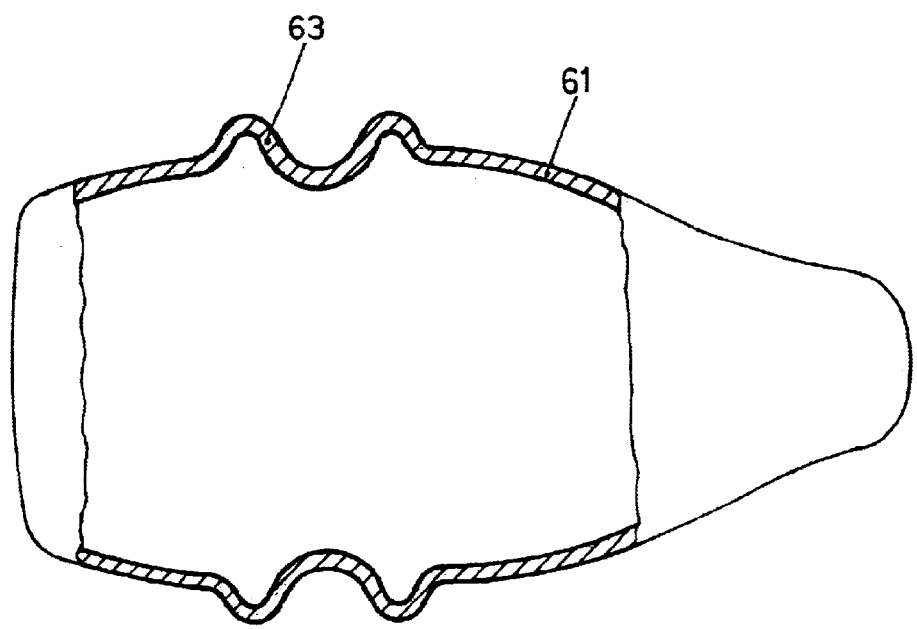
Figure 22:
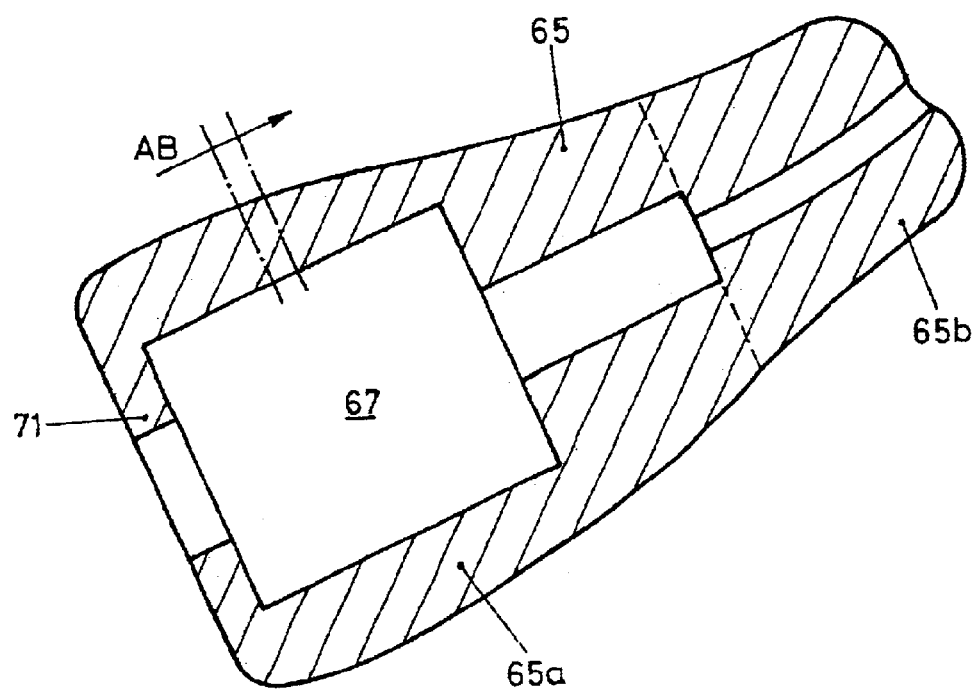
Figure 23:
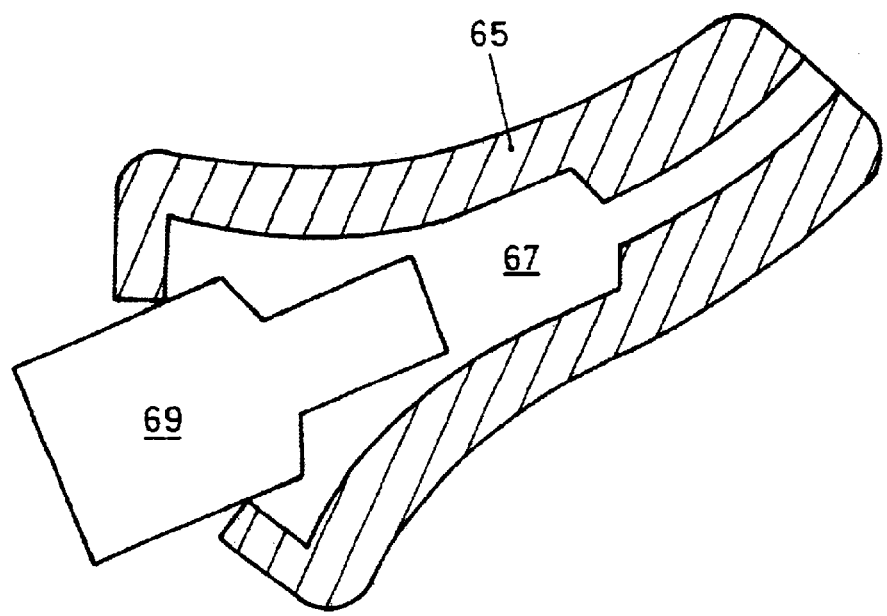
Figure 24:
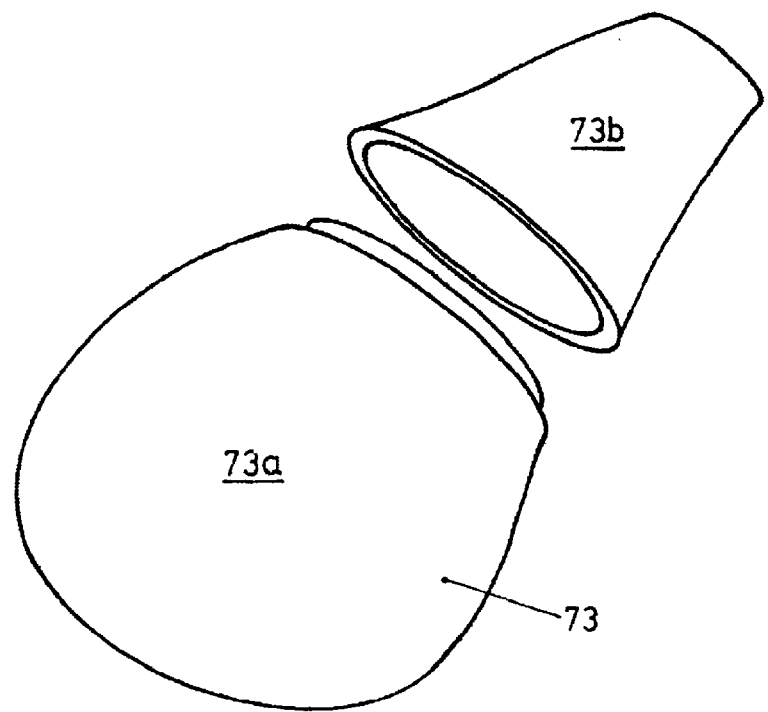
Figure 25:
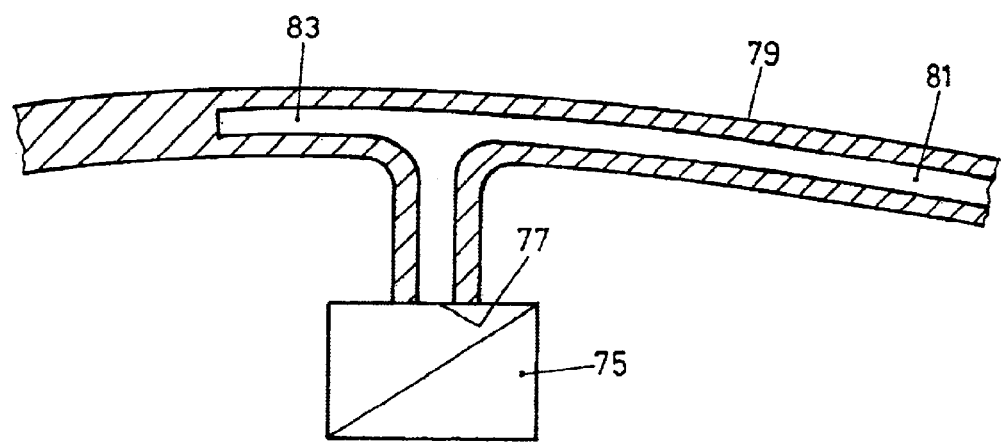
Figure 26:
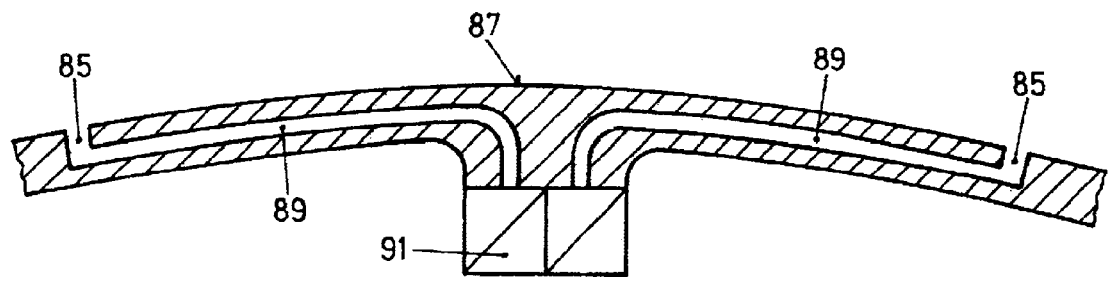
Figure 27:
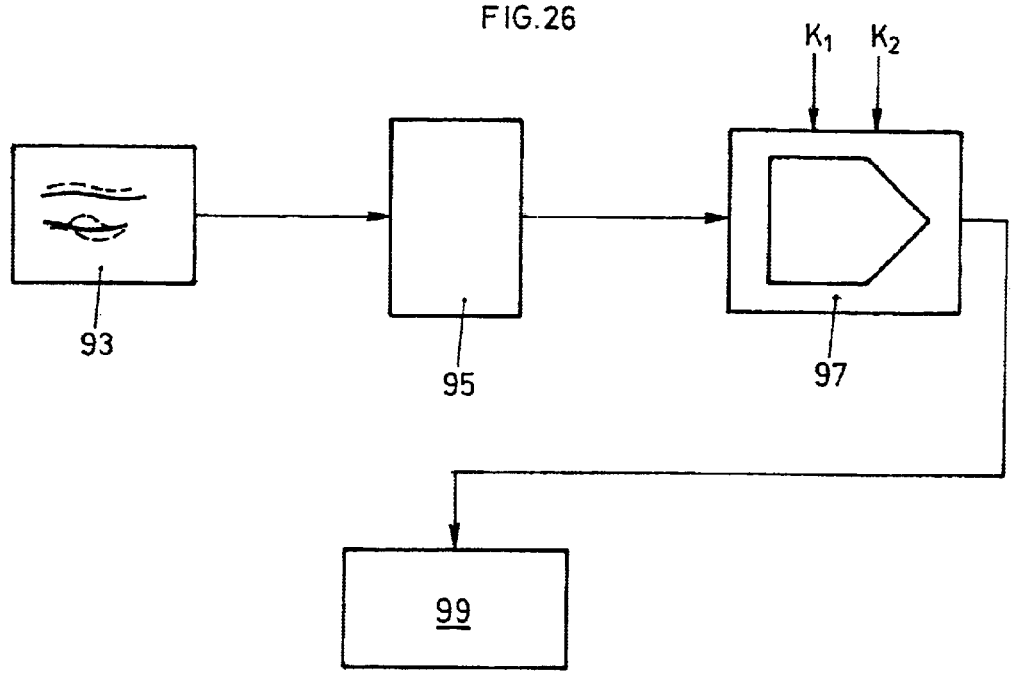
Figure 28:
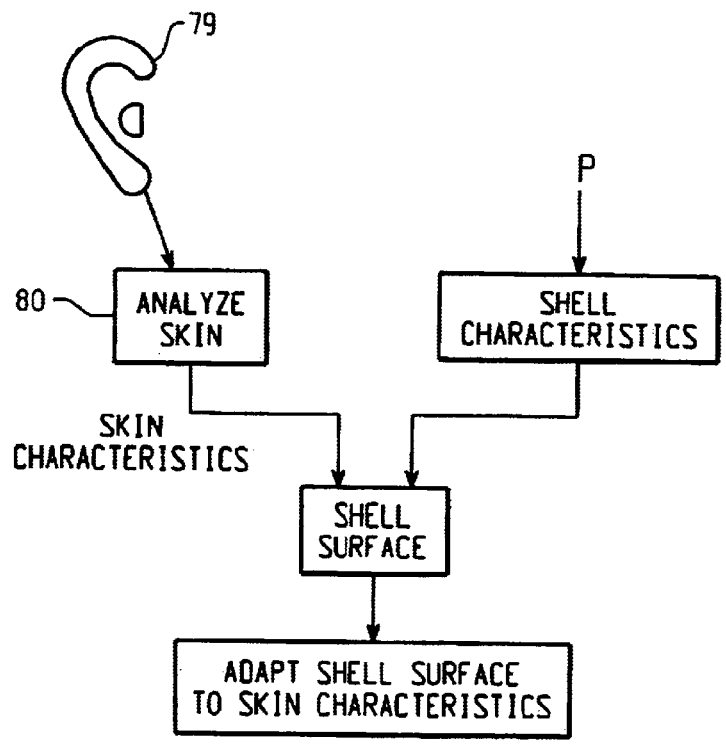
Figure 29:
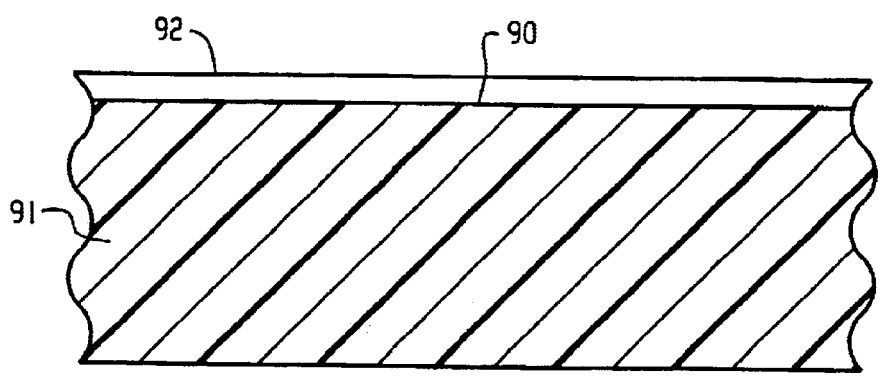
Figure 30:
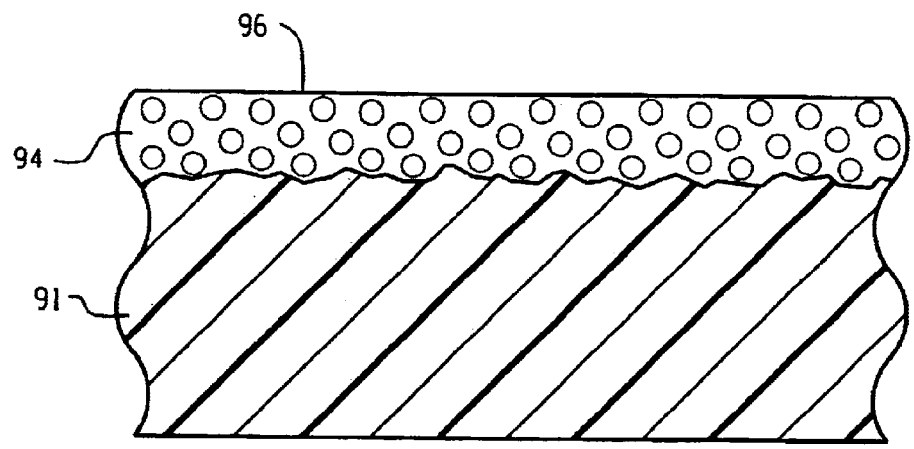
Figure 31:
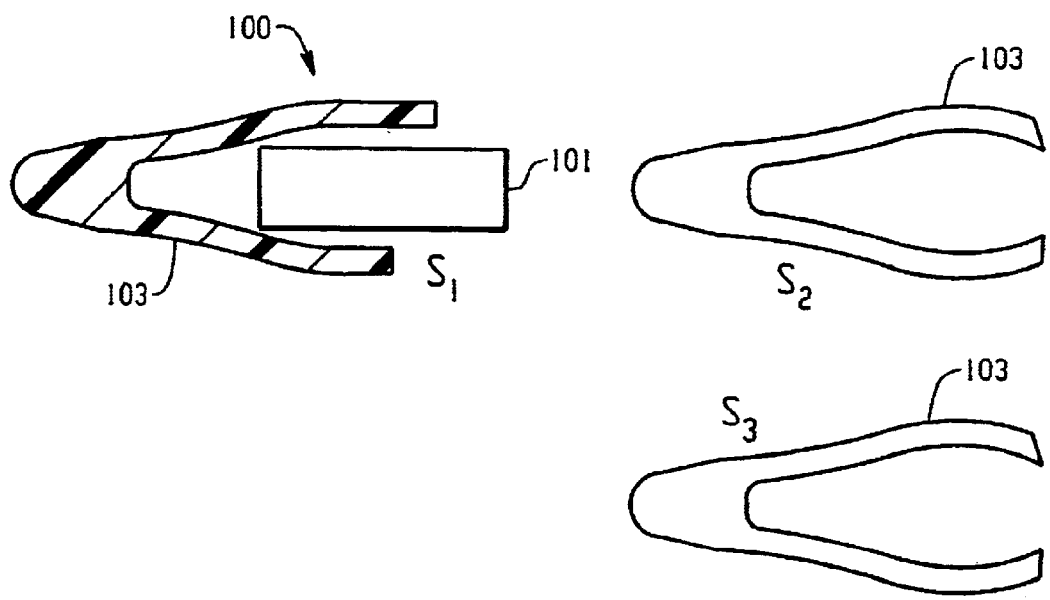

FIG. 4 schematically shows an in-ear hearing aid with a prior art earwax protection cap;

FIG. 5 is a view in analogy to that of FIG. 4 of an in-ear hearing aid with an earwax protection cap manufactured with the method according to the present invention;

FIG. 6 is an in-ear hearing aid with a conventional venting slot worked therein;

FIGS. 7(*a*) to 7(*f*) show perspective cutaways of the surfaces of ear devices comprising venting slots manufactured with the method according to the present invention;

FIG. 8 is a schematic cutaway of an ear device surface comprising a venting slot of varying cross-sections and cross-sectional shapes considered along its longitudinal extent and as manufactured by the method according to the present invention;

FIG. 9 schematically shows an in-ear ear device comprising a venting slot of increased length extent and as manufactured by the method according to the present invention;

FIG. 10 is a view in analogy to that of FIG. 9 of an in-ear ear device with several venting slots as manufactured by the method according to the present invention;

FIGS. 11(*a*) to (*e*) are cutaways of ear device shells fitted with venting channels of various cross-sectional shapes and dimensions and as manufactured by the method according to the present invention;

FIG. 12 is a view in analogy to that of FIG. 8 of a venting channel in an ear device with a longitudinally varying cross-sectional shape or area respectively and as manufactured by the method according to the present invention;

FIG. 13 shows in analogy to FIG. 9 schematically an in-ear ear device with a venting channel of increased extent and as manufactured by the method according to the present invention;

FIG. 14 is a view in analogy to that of FIG. 10 of an in-ear ear device with several venting channels and as manufactured by the method according to the present invention;

FIG. 15 schematically shows a longitudinal section of an in-ear ear device with a ribbed inner surface;

FIG. 16 is a cross-sectional cutaway of the ear device of FIG. 15, the ribs being of different cross-sectional areas;

FIG. 17 is a perspective cutaway of an ear device shell with inside ribs as shown in the FIG. 15 or 16, whereby the ribs vary in their cross-sectional shape and dimension along their length extent;

FIG. 18 is a view in analogy to that of FIG. 15 of an in-ear ear device with outer ribs and as manufactured by a method according to the present invention;

FIG. 19 schematically shows a cutaway of a ribbed ear device shell with ribs of different cross-sectional area;

FIG. 20 schematically shows a cross-section of an ear device with outer or possibly inner ribs and with an inside space which is at least partially filled with a filler material;

FIG. 21 schematically shows a cutaway of a longitudinal section of an ear device shell comprising a part which is flexible as concerns bending and compression and as manufactured by the method according to the present invention;

FIG. 22 is a schematic longitudinal section of an ear device shell comprising a receiving space for an electronic module and as manufactured by the method according to the present invention;

FIG. 23 shows the ear device shell of FIG. 22 being urged over an electronic module;

FIG. 24 is a schematic perspective view of an in-ear ear device, in particular of an in-ear hearing aid device with a two-part, separable and assemblable device shell as manufactured by the method according to the present invention;

FIG. 25 shows in a schematic cutaway representation the integration of acoustic conductors and matching members to an acoustic/electric or to an electric/acoustic transducer within an ear device and as manufactured by the method according to the present invention;

FIG. 26 shows in a representation in analogy to that of FIG. 25 the configuration of two or more than two acoustic conductors in the shell of an ear device and manufactured according to the method according to the present invention;

FIG. 27 shows by means of simplified signal-flow/functional-block-diagram a novel method or a novel arrangement respectively to carry out such method, wherein account is taken of the dynamics of the area of application of an ear device when shaping such device, FIG. 28 by means of a simplified flow diagram, a technique for manufacturing a hearing device under close consideration of skin characteristics at individual's application area;

FIG. 29 by means of a section of the shell of a hearing device, a first preferred embodiment of adapting the shell's surface to skin characteristics of individual's application area;

FIG. 30 in a representation according to FIG. 29, a second embodiment of appropriately tailoring and manufacturing the said shell surface area;

FIG. 31 schematically, a further preferred embodiment of flexibly exchanging the shell of a hearing device to adapt its surface characteristics to the instantaneous needs of the individual with respect to skin at the application area.

Preferably all embodiments of ear devices described subsequently to the manufacturing method are made using the method as outlined below.

DEFINITION

We understand by the expression "ear device" a device which is applied adjacent to the outside of the external ear and/or to the external ear and/or in the auditory canal. Such devices include outside-the-ear hearing aids, in-ear hearing aids, earphones, noise-protection and water-protection inserts etc. Such devices may thus be active or passive i.e. with built-in electronic devices or without it. Their outer shape is partly fitted to the area of the body, adjacent or in the ear, where they are to be applied. In German such ear devices are known as "Otoplastik".

1. Manufacturing Process

The preferred manufacturing method for the ear devices described individually below rests on 3D digitizing the shape of an individual's particular application area for the ear device and then realizing the ear device or the shell thereof by an additive built-up process. Additive built-up processes are also known as "rapid prototyping". References to such additive built-up processes as already used in rapid prototyping may be found at/in http://ltk.hut.fi/~koukka/RP/rptree.html (1) and Wohler's Report 2000, Rapid Prototyping & Tooling State of the Industry (2)

Out of the group of presently known additive built-up processes for rapid prototyping laser sintering, laser- or stereolithography or the thermojet process are especially applicable to construe ear devices or their shells, thereby especially the embodiments thereof as described below. The specifications of these preferred additive built-up processes shall be discussed now only in brief, summarizing manner:

Laser Sintering: Hot-melt powder is deposited in a thin layer on a powder bed, e.g. using a roller. The powder layer is solidified using a laser beam which is controlled according to the shape of a sectional layer of the ear device or of the shell of such ear device, thereby making use of the 3D shape data of the individual application area. A solidified sectional layer of the ear device or of its shell is thus produced within the remaining loose powder. This layer is then lowered from the powder plane and a new powder layer is deposited on it, which is again laser-solidified according to a subsequent sectional layer of the ear device.

Laser- or Stereo-Lithography: A first sectional layer of an ear device or of its shell is solidified by a UV laser at the surface of a liquid photopolymer. The solidified layer is lowered and is covered again with liquid polymer. Using the UV laser, a second sectional layer of the ear device or of its shell is solidified on top of the already solidified layer. Again laser position control is performed by means of the 3D data or information of the previously recorded individual application area, among other data controlling the laser.

Thermojet Processing: The contour formation according to the sectional layers of the ear device or of its shell are implemented similarly to an ink jet printer by deposition of liquid according to the digitized 3D shape data, especially of the individual application area. Thereafter the deposited sectional "drawing" is solidified. Again, following the principle of additive build-up, layer after layer is deposited so as to finally build up the ear device or its shell. The following documentation is referred to regarding other additive built-up processes and regarding the above mentioned preferred ones:

http://www.padtinc.com/srv_rpm_sls.html (3)

"Selective Laser Sintering (SLS) of Ceramics", Muskesh Agarwala et al., presented at the Solid Freeform Fabrication Symposium, Austin, Tex., August 1999, (4)

http://www.caip.rutgers.edu/RP_Library/process.html (5)

http://www.biba.uni-bremen.de/groups/rp/lom.html or http://www.biba.uni-bremen.de/groups/rp/rp_intro.html (6)

Donald Klosterman et al., "Direct Fabrication of Polymer Composite Structures with Curved LOM", Solid Freeform Fabrication Symposium, University of Texas at Austin, August 1999, (7)

http://lff.me.utexas.edu/sls.html (8)

http://www.padtinc.com/srv_rpm_sla.html (9)

http://www.cs.hut.fi/~ado/rp/rp.html (10)

Principally the additive built-up processes always deposit a thin layer of material on a surface, be it as a full surface as is the case in laser sintering or stereo lithography, be it already as a contour of a sectional layer of the ear device or of its shell under construction. Thereupon the desired sectional shape is stabilized, i.e. solidified.

Once one layer has been solidified, a new layer is deposited on it as was described, and this new layer in turn is solidified and thereby joined to the layer underneath it, which was already finished before. In this manner the ear device or its shell is construed by additive layer by layer deposition.

For industrial manufacturing, preferably not only the sectional layer of one individual ear device or of its shell is deposited or solidified, but several of such individual devices or shells simultaneously. When laser sintering e.g. the one laser which commonly is mirror controlled, sequentially solidifies the sectional layers of several ear devices or of their shells before all these solidified sectional layers are commonly lowered. Thereupon and following up deposition of a new layer of powder across all already solidified and lowered sectional layers, the several further sectional layers are realized. In spite of this parallel manufacturing the particular ear devices or the particular shells thereof are manufactured individually and individually digitally controlled.

Thereby, a single laser beam is used to solidify the several sectional layers and/or more than one beam are operated in parallel and are controlled in parallel.

In an alternative of this procedure one laser solidifies one sectional layer while simultaneously the powder layer for the formation of another ear device or shell thereof is deposited. Thereupon the one laser solidifies the prepared powder layer according to the sectional layer for the further device while the previously solidified layer is lowered and a new powder layer is deposited thereon. Thus the laser operates intermittently between two or more ear devices or their shells being built up, the laser down time caused by the powder deposition when forming one of the shells being exploited to solidify a sectional layer of another ear device being built up.

Figure 1:
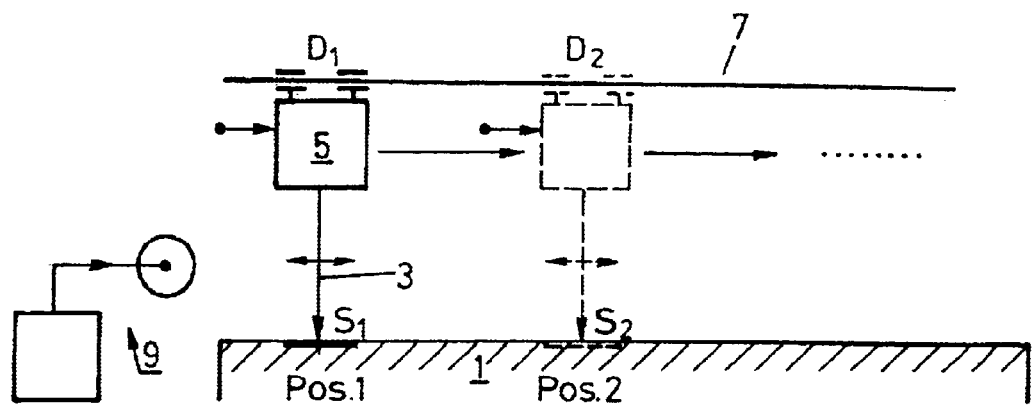
FIG. 1 is a simplified functional block diagram of a manufacturing plant operating on the method according to the present invention, thereby optimizing industrial manufacturing of ear devices.

FIG. 1 schematically shows how, in one embodiment, several ear devices or their shells are industrially manufactured in parallel processing, using laser sintering or laser- or stereolithography. A laser with a control unit 5 and a beam 3 is mounted above the bed 1 for powder or liquid medium. In position 1 the laser solidifies the layer $S_1$ of a first ear device or of its shell while being controlled by a first individual set of data, $D_1$. Next the laser is moved by a conveying device 7 into a second position where by means of the individual data set $D_2$ it produces the layer $S_2$ corresponding to a further individual contour. Obviously several lasers can be moved together as one unit and accordingly more than one individual ear device can be produced simultaneously. Only after the lasers 5 have produced the particular individual layers in all the positions, a new layer of powder is deposited by means of a powder supply indicated in general manner by 9, when laser sintering is used, while (not shown in the figure) when laser- or stereolithography is used, the solidified layers S are lowered in the bed of liquid.

Figure 2:
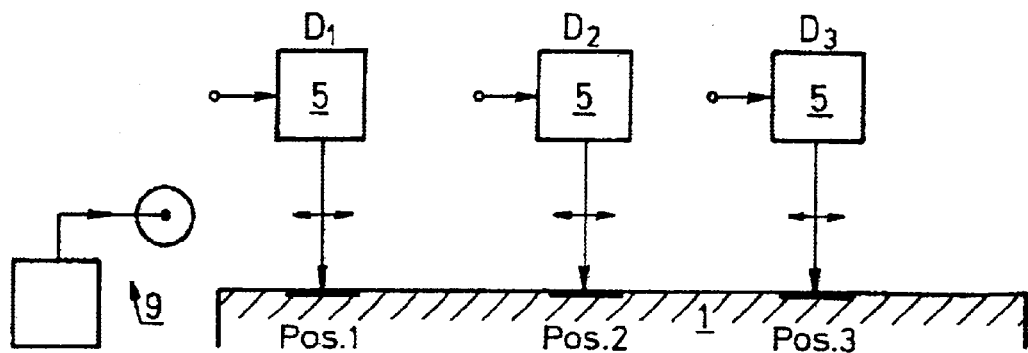
FIG. 2 is a view in analogy to that of FIG. 1 of a further embodiment of such a plant.

As shown in FIG. 2 sectional layers of individual ear devices or of their shells are solidified simultaneously at one or several liquid or powder beds 1 by means of simultaneously and individually controlled lasers 5. Following this solidification and after shutting off the lasers, the powder source 9 again deposits a new layer of powder, whereas in the case of laser- or stereolithography the just solidified sectional layers or the already solidified build-ups are lowered into the liquid bed.

Figure 3:
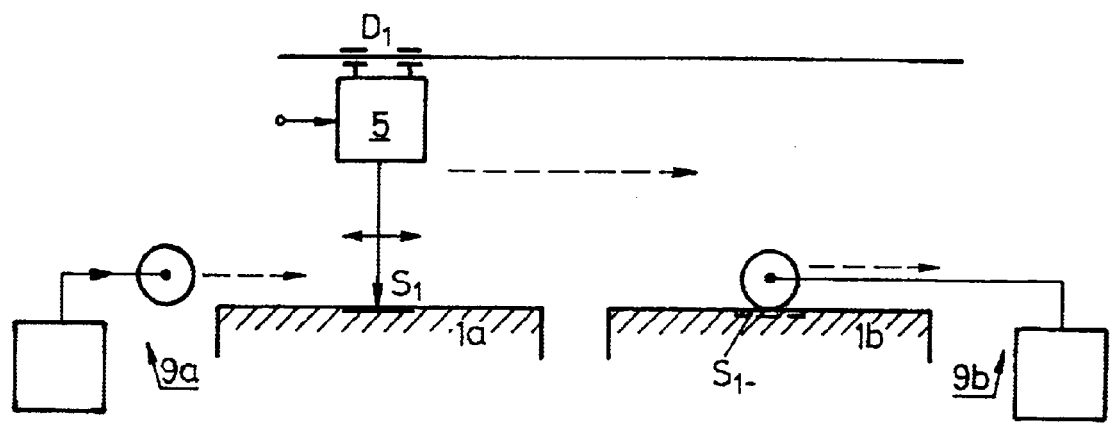
FIG. 3 is a view in analogy to those of the FIGS. 1 and 2 of a still further embodiment of the plant.

According to FIG. 3 the laser 5 solidifies the layer $S_1$ at the one powder or liquid bed $1a$ and then switches over to the bed $1b$ (dashed lines), where, during the solidification cycle at bed $1a$, the powder depositing source $9b$ deposits powder over a previously solidified layer $S_1$, or, as regards laser- or stereolithography, the layer $S_1$ is being lowered. Only when the laser 5 becomes active at the bed $1b$ the powder source $9a$ deposits a new layer of powder over the just solidified layer $S_1$ at the bed $1a$, or the layer $S_1$ is lowered in liquid in the bed $1a$.

When using the thermojet process and in order to similarly increase productivity, sectional layers of more than one ear device or of their shells are simultaneously deposited, i.e. in one stroke by one deposition head, or, when in parallel, by several such heads.

The above discussed method allows implementing highly complex shapes of ear devices or of their shells, both as regards their external shape with individual matching to the application area and, as regards a shell, its inside shape. Overhangs, recesses and protrusions are easily implemented.

Moreover materials are known for additive built-up processes which can be shaped into rubbery, elastic and yet shape-stable shells which, where desired, may vary locally in wall thickness down to extremely thin walls while nevertheless being resistant to tearing.

In a presently preferred implementation, the digitizing procedure of the individual application area, in particular that of hearing aids, and even more that for in-ear hearing aids, is carried out in a specialized facility, in the latter case at the audiologist. In the form of 3D information, the individual shape is recorded there—especially in relation to hearing aids—and is transmitted to a production center, be it by transmitting a data storage medium, be it by an internet connection etc. Particularly using the above mentioned procedures, the ear device or its shell and specifically the in-ear hearing aid shell is shaped at the production center. Preferably the final assembly of the functional components is also carried out at this center.

Because, and as already mentioned, the thermoplastic materials which are used in general result in a relatively elastic, supple external shape, the shaping of ear devices or of their shells becomes much less critical with respect to pressure sites than has been experienced so far, and this feature is especially significant regarding in-ear ear devices. Illustratively, in-ear ear devices may be realized as hearing protectors, as earphones, as water-protection inserts and especially as in-ear hearing aids, which may be introduced similarly to rubbery plugs and of which the outer surface optimally applies the shape of the application area, namely of the auditory canal. One or more venting ducts or channels can easily be fitted into the in-ear ear devices, so that as the ear device may be seated in a sealing manner in the auditory canal, eardrum ventilation is kept undegraded. Moreover the device's inside space can be optimized and be optimally utilized due to the individual 3D data or the application area, even individually as regards any individual apparatus configuration to be received in the device as in the case of a hearing aid.

In particular as regards ear devices in the form of hearing aids, the centralized manufacturing of their shells allows central storing and managing of individual data relating to the individual shape of the application area and also of the individual functional components and their adjustment. If for any reason a shell must be replaced, it can be readily remanufactured by retrieving the individual data sets without the heretofore necessary laborious new matching process.

Considering that the described procedures for manufacturing ear devices are known, but only for rapid prototyping and are described in the literature, they need not be discussed herein in all their technical details.

Surprisingly, however, by taking these known rapid prototyping techniques over into industrial and commercially acceptable manufacturing of ear devices, very substantial advantages are attained on grounds which per se are not significant in rapid prototyping, for instance the elasticity of the thermoplastic materials, the possibility to individually create exceedingly thin walls, etc.

In summary, the use of the cited additive built-up processes in manufacturing of ear devices or of their shells makes it possible to integrate thereat various functional elements which are laid out at the computer when designing the ear device and which are integrally produced as the ear device or its shell is built up. Conventionally such functional elements have been fitted into or joined to the finished ear device or to its shell, which may be recognized by material interfaces or by inhomogeneities in the material at link areas of such components to e.g. the shell.

As regards the cited ear devices, especially those provided with electronics such as hearing aids, and especially in-ear hearing aids, components which can be directly integrated by the proposed technique into the ear device or its shell are e.g. seats and fasteners for components, ear-wax protection systems, venting channels or grooves for in-ear ear devices, supports which position in-ear ear devices in the auditory canal as so-called claws or channel locks.

FIG. 4 illustrates in a schematic manner an in-ear ear device 11, e.g. an in-ear hearing aid, at which the acoustic output 13 to the ear drum is protected by an earwax protection cap 15. This protection cap 15 heretofore has been mounted during manufacturing as a separate part onto the shell 16 of the ear device 11, being affixed e.g. by gluing or bonding. As shown in a similar view in FIG. 5, when using the above mentioned additive built-up processes, the earwax protection cap 15a is directly integrated to the shell 16a of the otherwise identical in-ear ear device 11a. At the link area schematically denoted by P in FIG. 4, where, in the conventional technique, necessarily an inhomogeneity in the material is present, or a material interface, this is not the case in the embodiment of FIG. 5: The material of the shell 16a transits homogeneously into that of the earwax protection cap 15a.

The above description is merely an illustrative example of the manner in which known earwax protection systems and other functional elements may be integrated using the manufacturing technique as was described above.

Several specific and novel ear devices are now discussed below:

2. Vented In-ear Ear Devices

It is known to provide an external venting slot in in-ear ear devices, in particular in in-ear hearing aids, in the manner as schematically shown in FIG. 6. Such venting slots being used today are not at all optimal under several aspects:

With respect to acoustical behavior: The presently known venting slots hardly match the particular acoustical requirements. In active ear devices, for instance in-ear hearing aids, they can hardly contribute to solve the feedback problem from the electro/mechanical output transducer to the acoustical/electrical input transducer.

Even as regards passive in-ear ear devices, such as hearing protection devices, they are unable to support the desired protective effect and simultaneously to maintain the desired venting properties.

Sensitivity to earwax: Presently used venting slots in the outside surfaces of in-ear ear devices are exceedingly sensitive to earwax formation. Depending on its intensity, such earwax formation may rapidly degrade the venting slots in their venting abilities, and may even clog them entirely.

For in-ear ear devices, thereby especially for in-ear hearing aids or for hearing protection devices, but also for ear devices, which only partly enter the auditory canal, such as earphones, venting systems are now presented which at least partly remedy the drawbacks of known systems.

Thereby a distinction is made between different venting systems, namely:

those which are at least partly open towards the wall of the auditory canal, similarly to slots, those which are fully closed towards the wall of the auditory canal.

2a) Venting Systems Open Towards the Wall of the Auditory Canal

FIGS. 7(a) through (f) show schematic and perspective representations of cutaways of the outer wall 18 residing in the auditory canal of an in-ear ear device with novel venting-slot profiles. According to FIG. 7(a) the cross-sectional profile of the venting slot 20a is rectangular or quadratic and constrained to predetermined, accurately maintained dimensional ratios. As shown in FIG. 7(b), the cross-sectional profile of the venting slot 20b has the shape of the sector of a circle or of an ellipse, again constrained by accurately predetermined cross-sectional edge curve 21b. By precisely predetermining and implementing the cross-sectional contour of the venting slots 20, some predictability and control of the acoustical transmission behavior along this slot when resting against the inner wall of the auditory canal may already be attained. Obviously the acoustic behavior also depends on the length subtended by the slot 20 along the outer wall 18 of the ear device.

In the FIGS. 7(c) through (f) further venting slots cross-sectional profiles are shown, which additionally are protected against earwax. The profile of slot 20c according to FIG. 7(c) is in the form of a cross-sectional T.

With respect to the open cross-sectional slot bottom surface at 27c, the inwardly projecting parts 23c and the resulting constriction 25c pointing towards the wall of the auditory canal already provide a substantial protection against earwax influence. Even if earwax were to penetrate the constriction 25c and harden therein, the venting slot will not thereby be significantly constricted or even clogged, the slot then becomes a closed venting channel. The FIGS. 7(d) through 7(f) are based on the principle as shown in FIG. 7(c) and the cross-sectional shape of the open slot bottom parts 27d through 27f is shown in different geometries, namely being arcuate according to FIG. 7(d) or having the form of a sector of an ellipse, triangular according to FIG. 7(e) and circular or elliptical according to FIG. 7(f).

By appropriately designing the cross-sectional slot surface, which is shown in merely illustrative manner in FIGS. 7(a) through 7(f), substantial improvements may be attained relating both to acoustical properties and to protection against earwax as compared with conventional state of the art's haphazardly contoured venting slots. Thereby the profiles of the slots are now first computer modeled taking into account the protection against earwax and the acoustical effects and are integrated accurately into the ear devices as manufactured. The above discussed additive built-up processes are especially well suited for such purposes. In order to further optimize the acoustical effects of the venting slots, the most varied acoustical impedances may be implemented along the novel venting slots, which is as an example shown at the slot 29 of FIG. 8, which, propagating in its longitudinal direction, defines for different profiles, combined as desired and according to FIG. 8, from profiles according to FIG. 7.

Similarly to the configuration of passive electric circuits, the resultant acoustical transfer behavior of the slot abutting the auditory canal can be computer modeled and checked and then be integrated into the in-ear ear device or its shell.

One can provide sections of the device which are provided with an increased earwax protection there where such sections are especially exposed to earwax, as is shown in FIG. 8 at A.

Furthermore, it might be highly desirable, especially with an eye on optimizing the acoustical behavior, to tailor the venting slots longer than would be possible from the actual length of a particular in-ear ear device. As shown in FIG. 9 this goal is attained in that such slots 31, realized as e.g. shown in FIGS. 7 and 9, run along predetermined curves along the surface of the ear device, for instance as shown in FIG. 9, practically as slots helically wound around the ear device. Additional flexibility of optimization is reached in that more than one venting slot are run along the ear device surface as schematically shown in FIG. 10. Because of the high design flexibility reached, regarding the venting slots, such slots may be differently dimensioned according to the respective application area in the auditory canal, with respect to earwax protection and to acoustical behavior and thus may be realized in an optimized manner along the surface of an ear device.

2b) Venting Systems With Fully Integrated Channels

This embodiment of the novel venting system is based on venting channels which at least along parts thereof are fully integrated into the ear device and which are thus closed there towards the wall of the auditory canals. This system will be elucidated below in relation to its realization in the shell of an ear device. It must be nevertheless emphasized that when no further unit needs to be integrated into an ear device and such ear device is tailored as a full material device the discussion below is also valid for channels which are provided through such full material devices.

FIG. 11 shows in analogy to FIG. 7 different cross-sectional shapes and relations of cross-sectional areas of proposed venting channels or ducts 33a through 33e. As shown in FIG. 11(a) the cross-sectional contour of the venting channel 33a in the shell of the ear device is rectangular or quadratic. In the embodiment of FIG. 11(b) the cross-section of the channel 35b has the shape of a sector of a circle or of an ellipse. In the embodiment of FIG. 11(c) the cross-section of the venting channel 33c is circular or elliptical, whereas it is triangular in the embodiment according to FIG. 11(d).

In the embodiment of FIG. 11(e) the shell of the ear device exhibits a complex inside shape, for instance has an integrated support part 37. To optimally use the available space, the venting channel 35e of this embodiment is designed with a cross-sectional contour which exploits the complex shape of the shell of the ear device. As a result its cross-sectional shape runs in a complex manner partly into the support strip 37 integrated in the shell 35e.

Returning to the embodiment according to section 2a), it may be noted that such complex cross-sectional shapes optimally exploiting the available space may also be realized at venting slots which are open towards the auditory canal and as well, vice-versa, channel layout may be realized for closed venting channels as shown, for open slots, in the FIGS. 9 and 10.

Finally, FIG. 12 shows an embodiment of a fully integrated venting channel 39 which has along its length extent and as shown e.g. within the shell of the ear device, different cross-sectional shapes and/or extents of cross-sectional areas, as a result of which different acoustical impedances are implemented so as to optimize the acoustical transfer behavior. Be it borne in mind in this respect and in context with section 5) below, that because complex acoustical impedances may be realized, venting channels or slots, but especially closed channels as addressed in this section of the description, can easily be utilized simultaneously and at least along parts thereof as acoustical conductor segments at the output side of active electromechanical transducers, as e.g. at the output side of microphones, e.g. in in-ear hearing aids.

In analogy to the FIGS. 9 and 10, FIGS. 13 and 14 show how, on one hand, the integrated venting channels as described in this section of the description, can be extended by selecting a commensurate path along a respective ear device 43 and, on the other hand, how two or more such channels, where appropriate fitted with different and/or varying channel cross-sections, in analogy to FIG. 12, can be integrated in the ear device.

By the design shown in the sections 2a) and 2b), which are combinable according to respective needs, the expert is given access to a huge number of embodiment variations of novel venting systems and in particular to a large number of degrees of freedom on account of the different parameters each dimensionable per se to individually create optimal protection against earwax and optimal acoustical transfer behavior for respective individual ear devices. In all embodiments preferably the specific individual system configuration is calculated or computer modeled to meet the cited requirements. Thereupon the individual ear device is manufactured. Again the initially cited additive built-up processes, as known for rapid prototyping, are especially appropriate, controlled by the optimized modeling result.

3. Ear Devices Optimized With Respect to Shape Stability

This section discloses novel ear devices optimally matching the dynamics of the sites of use, i.e. the application area. It is e.g. known that conventional in-ear ear devices cannot meet the requirements of the comparatively large movement dynamics of the auditory canal for instance during chewing, because they exhibit substantially the same shape stability all along the device. Similarly e.g. the acoustical conductors between outside-the-ear haring aids and the auditory canal cannot freely follow the movement dynamics of the application area. The same problems, even if partly less pronounced, also arise with hearing protection devices, with earphones, water-protection inserts etc. In particular their intrinsic function, namely protection, will be partly degraded when increased account is taken of the movement dynamics of the application areas. Such is the case e.g. with known hearing protection devices made of elastically shape-changing plastics which meet well the cited dynamics of the application area, but as a tradeoff against their acoustical transfer behavior.

FIG. 15 schematically shows a longitudinal section of an in-ear ear device, whereas FIG. 16 shows a schematic cross-section of a segment of this ear device. The ear device, e.g. for receiving electronic components, comprises a shell 45, which is elastic, stocking-like, of thin-walled material. The shape stability of the shell skin, which in this embodiment is smooth on its outside, is assured, where desired, by ribs 47 integrated at the inside of the shell and being of the same material as the shell-skin.

Depending on the required dynamics for the ear device on one hand, for instance in order to take into account the dynamics of the auditory canal and on the other hand on the requirements relating to the support and the protection of components installed, as e.g. at an in-ear hearing aid, local distribution of the wall thickness of the shell skin 45, the density and shape of ribs 47 provided will be first computed and thereupon the ear device is realized on the basis of the computed data. Again the above mentioned manufacturing processes using additive built-up are exceedingly appropriate to this purpose. Obviously too the above discussed in-ear ear device design may be combined with a venting system as elucidated in relation with the FIGS. 7 through 14. In particular the ribs controlling dimensional or shape stability as e.g. bending behavior in given zones of the ear device may be fitted with different cross-sectional contours, and may transit where necessary from one contour into another as propagating along their longitudinal extent.

FIG. 17 is a perspective view schematically illustrating the design of the outer skin 45 fitted with ribs 47 of varying cross-sectional areas along their longitudinal extents.

In lieu of or complementing the desired wall reinforcement and the design of the desired flexural or torsional behavior, in short the shape behavior of in-ear ear devices, the inner rib pattern can be complemented as shown in FIGS. 17 and 18 by an external rib pattern. For that purpose and as shown in FIGS. 18 and 19, a pattern of ribs 51 is manufactured on the outside of the ear device 49, where called for, with zones of varying density, direction and cross-sectional profile.

As shown in FIG. 19 such complementation may be implemented in ear devices with a cavity, but also in ear devices lacking such cavities, which do not hold e.g. electronic components, namely e.g. in hearing protection and in water protection ear devices. Such an ear device is shown in a schematic cross-sectional view in FIG. 20. Therein the inside space 53 consists of an extremely compressible absorbing material which is enclosed by a shape-subtending shell skin 55 which is provided with the rib pattern 57. Both the "skin" 55 and the rib pattern 57 are jointly and integrally manufactured. Again the initially cited manufacturing processes are appropriate for this purpose, with resort to additive built-up techniques. To what extent in the near future such additive built-up processes can be implemented on one workpiece while changing the processed materials remains to be seen. If it should become possible to do so, it will be feasible, for instance as regards the embodiment of FIG. 20, also to build up the filler 53 simultaneously with the shell skin 55 and the ribs 57 as a respective sectional layer.

FIGS. 18 and 19 in particular show that by means of the external rib pattern, it is possible to simultaneously form venting slots or free venting spaces as indicated in schematic and illustrative manner by the arrow P.

As regards FIG. 20, if required and as indicated by dashed lines at $57_i$, it is quite feasible to fit the shell skin 55 with an inner rib pattern $57_i$ even when the in-ear ear device is filled with material, that is when it is not intended to receive further components, for instance electronic ones. Furthermore and as indicated in dashed lines 59 in FIG. 20, ear devices also can be manufactured which leave free a cavity to receive units such as electronic components, but wherein the intermediate space between such a cavity 59 designed specifically for the required volumes and shapes of the additional elements to be integrated and the shell skin 55 is filled by e.g. a resilient or acoustically attenuating material, or wherein components to be installed are cast in place with such a material up to the shell skin 55.

The shell 55 or 45 of the FIGS. 15, 16 and 17 furthermore may be made of an electrically conducting material so that thereby the electronic components inside become electrically shielded. This feature also applies to the filling material 53 of FIG. 20.

By means of the FIGS. 15 to 20 an ear device was shown by the example of a in-ear ear device, the shell thereof being shape stabilized by inner and/or outer ribs, resulting in an extremely lightweight and controllably shapable construction. Obviously, such construction may also be applied as required to outside-the-ear ear devices.

FIG. 21 shows another embodiment of an-ear ear device which is made flextural or compressible in a predetermined region. The shell 51 of the ear device, in particular that of an in-ear hearing aid, for that purpose, is fitted in one or more predetermined areas with a corrugated or accordion-like bellows structure 63, where bendability or compressability are required. Even though this procedure is illustrated in FIG. 21 by means of the shell of an in-ear ear device, such a structure can be implemented easily and if required also for an outside-the-ear ear device. Again the initially cited manufacturing processes are preferably used for implementation. As already elucidated in relation with FIG. 20 the inside volume of this ear device can be filled too with a filler material corresponding to the particular requirements, or components installed therein can be embedded in such a filler material, as a result of which the device becomes more stable and has improved acoustical behavior.

4. Modular Housings/Installations

A problem arises in particular with in-ear hearing aids that the application area, namely the auditory canal, changes its shape. This is manifestly the case for growing humans. However, even in adults the auditory canals may also strongly change in parts, mostly with the tendency to form constrictions (e.g. the so-called diver's ear).

Accordingly, conventional in-ear hearing aids incur the problem that even if the installed components could be kept unchanged over many years, so that for instance only the transfer function of the hearing aid would have to be readjusted for the particular hearing conditions, nevertheless new hearing aids must be designed just on the account alone that the previous shaping no longer properly fits into the auditory canal.

The approach as was elucidated in section 3) already offers the possibility to improve on such drawbacks because they enable automatic shape matching of the ear device to changing shapes of the application areas. In the present section further measures shall be explained, in particular relating to in-ear ear devices. Be it borne in mind that the measures as of this section also allow changing the "housing" of outside-the-ear ear devices such as of outside-the-ear hearing aids, not only when required for comfort of wearing but also as desired, for instance to alter the esthetic appearance of such outside-the-ear hearing aids.

FIG. 22 schematically shows an in-ear ear device 65 in longitudinal section, the shape of the inside space 67 substantially corresponding to that of the electronic module 69 of FIG. 23 to be received in this inside space. The ear device 65 is made of an elastic material, and as shown in FIG. 23, can be urged over the electronic module 69. The inside space 67 is configured in such a way that the module(s) to be received are directly positioned and affixed in mechanically interlocking manner by the ear device 65. On account of such a procedure, it is easy to fit one and the same electronic module 69 with different ear devices 65 so as e.g. to account for the growth of the auditory canal of a child. With respect to the hearing aid, the ear device shell becomes so practically an easily exchangeable, disposable accessory part. The ear device 65 is easily exchanged not only to match changed conditions on the application area, but also merely for being soiled. This feature even can be used for instance in the event of external otitis, in medical applications, for instance to deposit medicines at the outer surface of the ear device or at least to insert sterilized ear devices at regular intervals.

The design shown in the FIGS. 22 and 23 of course may be combined with a design disclosed in the sections 2) and 3), and preferably the ear device 65 is manufactured by the processes discussed under section 1), thereby allowing configuring the most complex shapes to seat the module 69 without play and vibration-free.

As shown by the FIGS. 22 and 23, the phase plate 1, which otherwise is present in conventional in-ear hearing aids, is made integrally with the ear device. The same feature applies to further supports and to seats for the electronic components of the hearing aid. When implementing the layer-by-layer buildup processes discussed under section 1), as denoted in dashed pointed lines in FIG. 22 and in the built-up direction shown by the arrow AB, then it should be easily possible to manufacture the ear devices in said build-up direction AB from different materials and in relation to the needs in the particular zones. This feature also applies to the ear devices as discussed in sections 2) and 3) and as discussed in the following sections 5), 6) and 7). Thus, it is an easy matter at the example according to FIG. 22 to make the zone $65_A$ from an elastic material, whereas the output area $65_b$ is made of a shape-stable material.

FIG. 24 shows a further embodiment of an ear device, again in the form of an in-ear hearing aid as an example, allowing simple and quick exchange of installed components. Basically the design consists in manufacturing the ear device shell of an in-ear ear device subdivided into several parts, which may be assembled in the manner as e.g. shown in FIG. 24. Using quick connections, such as latches, pawl locks or even bayonet locks or the like, the housing or shell segments 73a and 73b of the in-ear ear device can quickly be mutually separated, the installed components such as electronic modules can be removed and may be inserted in another shell possibly with a different outer shape or principally in a new shell if this is necessary, for instance for cleaning or sterility reasons. If it is intended to discard the used shell, then it is clearly possible to design the shell part connection so that the shell can only be opened by its destruction, for instance in that externally not accessible locking elements such as latches are provided and the shell is just being cut open in order to remove the components.

Again this embodiment can obviously be combined with the heretofore described embodiments and with those still to be described.

5. Integrating Acoustical Conductors Into Ear Devices or Into Their Shells

Both as regards outside-the-ear as well as in-ear hearing aids, it is conventional practice to couple on one hand acoustical/electrical input transducers or electro/acoustical output transducers provided therein on their input side or their output side respectively by means of acoustical conductors, which are assembled as independent parts in the form of tubular structures, to, on the other hand, the ambient of the hearing aid or, in particular as regards the input acoustical/electrical transducer, to mount them with their reception surfaces adjacent to the surface of the hearing aid, possibly only separated by minor cavities and protecting devices towards the ambient.

Thereby when conceiving such hearing aids there is present a relatively large dependency, where in the hearing aid the converters and where in the hearing aid the coupling openings to the ambient are placed. It would be highly desirable to have largest possible conceptual freedom with respect to placing coupling openings to the ambient and placing the said converters or transducers within the hearing aid.

This goal is principally attained in that the acoustical conductors mentioned—at the input side of the acoustic/electrical converters or at the output side of the electrical to acoustical converters—are integrated into the ear device or in the wall of the ear device shell.

This feature is shown purely schematically in FIG. 25. A converter module 75 comprises an acoustical input or output 77. The shell 79 of the ear device of an in-ear or of an outside-the-ear hearing aid or of a headphone comprises, as an integral part, an acoustical conductor 81. This acoustical conductor is embedded at least to a part and as shown in FIG. 25 within the wall of the ear device shell 79. By means of acoustical stub conductors or conductor segments 83 preferably the respective acoustical impedance of the acoustical conductor 81 is matched. When applied to outside-the-ear hearing aids, this concept makes it possible to implement acoustical input apertures 85 distributed along the ear device and there where desired, and to couple such apertures via acoustical conductors 89, which are integrated in the ear device or its shell 87 to the acoustical/electrical converters 91 as provided and essentially independent therefrom, where such converters 91 are placed within the ear device. Thus in FIG. 26 there is e.g. shown how two converters are centralized to one module and their inputs are connected to the desired apertures 85 by acoustical conductors 89 respectively tailored. From consideration of the FIGS. 25 and 26 as well as of the explanations in section 2) with respect to the novel venting system it becomes apparent that it is absolutely possible to exploit venting channels additionally as acoustical conductor channels, especially if one accurately conceives the acoustical impedance conditions by means of acoustical matching members 83 as schematically shown in FIG. 25.

6. Identification of Ear Devices

When manufacturing ear devices, in particular in-ear ear devices, each is matched individually to its particular wearer. Therefore it would be extremely desirable to identify each finished ear device, thereby especially each in-ear ear device and thereby most particularly each in-ear hearing aid. Therefore it is proposed to provide within the ear device or within its shell an individual identification by means of intrusions and/or extrusions which besides of the individual purchaser may identify e.g. the manufacturer, may further define for a serial number of the product, may identify whether the device is to be worn on the left or on the right hand side. Such an identification is implemented most preferably during the manufacturing of the ear device with the built-up processes as were described under section 1). By such identification it is made sure that departing from manufacturing any mix up of devices is prevented. This is especially important for a subsequent possibly automated assembly with further modules, so e.g. during assembling of in-ear hearing aids. This procedure may obviously be combined with one or more than one of the procedures and aspects as described under the sections 2) to 5).

7. Optimizing Ear Devices With Respect to the Dynamics of the Area Where They are to be Applied When taking the shape of ear devices for in-ear applications, so e.g. for in-ear hearing aids, it is today customary to take from the auditory canal e.g. with silicon, a mold. Under consideration of the relatively large movement dynamics of the auditory canal, e.g. during chewing, it is evident that basing the shaping of the in-ear ear device practically on one instantaneous situation and making a mold in this situation may hardly lead to a result which may completely satisfy when wearing the resultant ear device. As is shown in FIG. 27 by means of a simplified functional block/signal-flow diagram, there is therefore taken from the dynamic application area, shown by block 93, the shape at several positions, which occur during the dynamics in practice. Thus there is registered, like a movie, the dynamics of the application area. The resulting data sets are stored in a storing unit 95. Even making use of customary procedures by taking molds, this novel procedure may be realized in that several molds are taken from the application area in two or more than two positions according to its dynamic in practice.

Subsequently such molds are scanned, and the respective digitalized data sets are stored in the storage unit 95. A further possibility e.g. resides to register the dynamics of the application area by means of x-rays.

In dependency of the accuracy to be reached several "pictures" or even a "movie" of the pattern of movement of the respective application area is registered. The data registered in the store unit 95 are subsequently fed to a computer unit 97. The output of the computer unit 97 controls the manufacturing process 99 for the ear device. If e.g., and as customary today, in-ear ear devices are manufactured with a relatively hard shell, the computer unit 97 calculates from the dynamic data as stored in unit 95 and possibly with the help of further manufacturing parameters as schematically shown at K the best fitting shape for the ear device so that an optimum comfort is reached when wearing the device in daily use and thereby maintaining its functional task. If the ear device is to be manufactured according to the section 3) of the description, the computer unit 97 calculates the characteristics of the different areas of the ear device with respect to flexibility, flexural behavior, compressability etc. At its output the computer unit 97 controls as was mentioned the manufacturing process 99, thereby preferably a manufacturing process as it was disclosed in section 1) as preferred manufacturing processes.

8. Adapting Outer Surface Characteristics of the Hearing Device Shell to the Application Area of the Individual for the Hearing Device In FIG. 28 there is schematically shown, by means of a functional block diagram, a further aspect of the present invention which was already addressed under point 4, "modular housings". When applying a hearing device to an individual's ear 79, being for an in-the-ear hearing device into the ear channel of the individual or for an outside-the-ear hearing device adjacent to individual's ear, characteristics of individual's skin at such application area should, under certain circumstances, be considered when manufacturing the hearing device for that individual.

(a) The color and the surface structure of the skin of the application area for the hearing device and of the skin adjacent to such area may be considered for conceiving the respective surface of the hearing device under the aspect of optimal aesthetic appearance of the hearing device once applied and of comfort for the individual carrying such hearing device.

(b) Mechanical characteristics of the skin and its underlying tissues as of bones or cartilage should be considered when manufacturing the shell of the hearing device, and especially its outer surface so as to ensure optimum comfort of the individual when carrying such hearing device.

(c) Chemical characteristics of the skin of the individual at and possibly adjacent to the application area for the hearing device as with respect to acidity, transpiration etc. should also be considered when tailoring the outer surface of the hearing device shell, and especially those parts thereof which come in intimate contact with the skin of the individual.

(d) The state of health of individual's skin at the application area or adjacent thereto, as e.g. with respect to already existing irritation, high dryness etc., should also be considered when tailoring the surface area of the hearing device shell, which comes into intimate contact with such individual's skin as the hearing device is applied to the individual.

Thus, summarizing, a single or multiple characteristics (a) to (d) of the skin at the application area of the individual, i.e. at that area, which comes in contact with the hearing device carried by the individual and possibly of areas just adjacent thereto, may be considered to make sure that the applied hearing device does not act as a disturbing factor for the individual under any of the addressed aspects.

According to FIG. 28 there is thus first defined the application area for the hearing device at the individual. According to block 80 the skin at that area is analyzed. This may be done by visual inspection, taking a probe etc. briefly by any known method of skin analysis. Thereby there is generated a skin analyzing result, which is significant for at least one of the following skin characteristics:

visual appearance as of color and of macro-structure,
micro-structure and texture
chemical characteristics as of acidity, dryness
health state as of irritation and abnormal dryness
mechanical characteristics as of underlying bone or cartilage structures.

Information of one and preferably more than one of the above mentioned skin characteristics is retrieved from skin analyzing 80 and applied for controlling surface manufacturing of the hearing device shell, especially along areas of said surface, which will be situated adjacent to or in intimate contact with individual's skin at the application area.

Manufacturing of the shell besides of such surface manufacturing is governed by other criteria P, as by geometric shape of the application area, intended use of the hearing device, modules to be built in etc.

At manufacturing 82 the surface area of the hearing device shell is manufactured to take into account visual appearance and possibly macro- and/or micro-roughness and texture of the skin by appropriately coloring and appropriately tailoring surface macro- and/or micro-roughness of the shell's surface area. This may be done by appropriately manufacturing such surface of the shell material, i.e. by appropriately tailoring its substantial rigid material surface.

For perfectly suiting chemical characteristics of the skin and of the health state of the skin, we propose to manufacture at 82 the surface of the shell to come in intimate contact with the application area's skin of the individual by applying a gel, a liquid or a pasteous substance to the surface of the shell. Such a substance, as an antibiotically acting substance or a neutralizing substance, may thereby be applied to the substantially rigid material of the remaining shell in that, as shown in FIG. 29 the solid material surface 90 of the shell 91 is roughened or structured, especially micro-structured, and there is applied a film 92 of the said liquid, gel or pasteous material.

An other possibility is, as shown in FIG. 30, to conceive at least the surface area of the solid shell material 30 to be porous and to fill such porous surface 94 with the respectively suited liquid, gel or pasteous substance to be slowly dispatched to the surface 96 of the shell 91 so as to realize long-term dispatching such substance to the skin of individual's application area.

Clearly, the state of the skin of individual's application area may change in time, which would necessitate differently manufactured surface areas of the shell. According to FIG. 31 there is provided at a hearing device 100, schematically shown, some parts or modules 101 upon which a shell 103 is removably applied as e.g. a stocking. There are manufactured such shells 103 with different characteristics $S_1, S_2, S_3$ of the surface coming in contact or being disposed adjacent to individual's application area, so that if there is need, the shell 103 of individual's hearing device, let's say with surface characteristics $S_1$, may easily be exchanged by an other shell 103 identical in shape, but with a different surface characteristics $S_2$ or $S_3$.

By this technique it becomes possible to optimally adapt the hearing device to individual's needs and thereby minimizing all uncomfort factors, which disturb the individual when carrying the hearing device. The hearing device may become a device for dispatching medicaments to the individual, especially via the skin of individual's application area. By appropriate tailoring of the shell's surface, especially at the contact area to individual's application area, any disturbing of the skin as of irritation thereof may be prevented in advance.

What is claimed is:

1. A method for manufacturing a hearing device to be applied to an application area of an individual's ear, said method comprising:

analyzing characteristics including at least one of chemical surface characteristics and of state of health of the skin of the individual's application area, thereby generating an analyzing result;

conceiving an outer surface of said hearing device to be applied to said application area as a function of at least a part of said analyzing result.

2. The method of claim 1, further comprising the step of conceiving an outer surface area of said hearing device as said function, which outer surface area is to be applied to said application area.

3. The method of claim 1, comprising the step of manufacturing said outer surface by applying to solid material at the outer surface of said hearing device at least one of a liquid substance, a gel-substance and a pasteous substance.

4. The method of claim 1, further comprising the step of generating as said analyzing result at least information about texture of said application area and adapting said outer surface area during said conceiving step to said texture.

5. The method of claim 1, further comprising the step of adapting said hearing device to changing characteristics of said skin of the individual's application area by providing at said hearing device a removable and re-applicable shell and adapting said outer surface of said hearing device by exchanging said shell with another shell adapted to changed characteristics.

6. The method of claim 1, further comprising the step of applying on the surface at least one of a medicament or an antibiotic.

* * * * *

UNITED STATES PATENT AND TRADEMARK OFFICE
CERTIFICATE OF CORRECTION

PATENT NO. : 7,014,010 B2 Page 1 of 1
APPLICATION NO. : 09/982290
DATED : March 21, 2006
INVENTOR(S) : Christoph Widmer It is certified that error appears in the above-identified patent and that said Letters Patent is hereby corrected as shown below:

IN THE SPECIFICATION:

In column 4, line 54, please delete "Tex" and insert --TX--

In column 10, line 58, please delete "haring" and insert --hearing--

In column 12, line 24, please delete "an-ear" and insert --an in-ear--

In column 14, line 15, after the word "have", please insert --the--

In column 17, line 16, please delete "An other" and insert --Another--

Signed and Sealed this

Twentieth Day of February, 2007

JON W. DUDAS
*Director of the United States Patent and Trademark Office*